United States Patent
Leunig

(10) Patent No.: US 8,216,157 B2
(45) Date of Patent: Jul. 10, 2012

(54) DEVICE FOR MEASURING THE INTERNAL ROTATION OF A HIP JOINT

(76) Inventor: Michael Leunig, Erlenbach (CH)

(*) Notice: Subject to any disclaimer, the term of this patent is extended or adjusted under 35 U.S.C. 154(b) by 1214 days.

(21) Appl. No.: 11/875,468

(22) Filed: Oct. 19, 2007

(65) Prior Publication Data
US 2008/0097456 A1 Apr. 24, 2008

(30) Foreign Application Priority Data
Oct. 23, 2006 (CH) .................................. 1690/06

(51) Int. Cl.
A61B 5/103 (2006.01)
A61B 5/117 (2006.01)
A61B 17/60 (2006.01)

(52) U.S. Cl. ......... 600/587; 600/595; 600/588; 606/102
(58) Field of Classification Search ............... 606/86 R, 606/102; 600/587, 591, 595; 482/51–148
See application file for complete search history.

(56) References Cited

U.S. PATENT DOCUMENTS

| | | | | |
|---|---|---|---|---|
| 5,913,835 A * | 6/1999 | Naoi et al. | .................. | 600/595 |
| 6,595,904 B1 * | 7/2003 | Staffa | .................. | 482/123 |
| 6,692,447 B1 * | 2/2004 | Picard | .................. | 600/587 |
| 6,773,376 B2 * | 8/2004 | Dvir | .................. | 482/8 |

FOREIGN PATENT DOCUMENTS
JP 2004-97489 4/2004
* cited by examiner

Primary Examiner — Thomas C. Barrett
Assistant Examiner — Matthew Lawson
(74) Attorney, Agent, or Firm — Rankin, Hill & Clark LLP

(57) ABSTRACT

Device for measuring the internal rotation of a hip joint, whereby the following steps are performed:
a) Positioning a person to be examined (1) on the seating surface (8) of a chair-like positioning aid (5) in a sitting position;
b) Fixating at least one of the upper thighs to be examined (3) of the person (1) on the seating surface (8) against translational motions, so that a rotation of the upper thigh (3) around its longitudinal axis is still possible;
c) Moving the corresponding lower thigh (4) across the sagittal plane (20) by using a force K of a constant value Z acting on the lower thigh (4), so that the distal end of the lower thigh (4) is deviated from the sagittal plane; and
d) Measuring the angle α between the sagittal plane (20) and the longitudinal axis of the lower thigh (4).

9 Claims, 1 Drawing Sheet

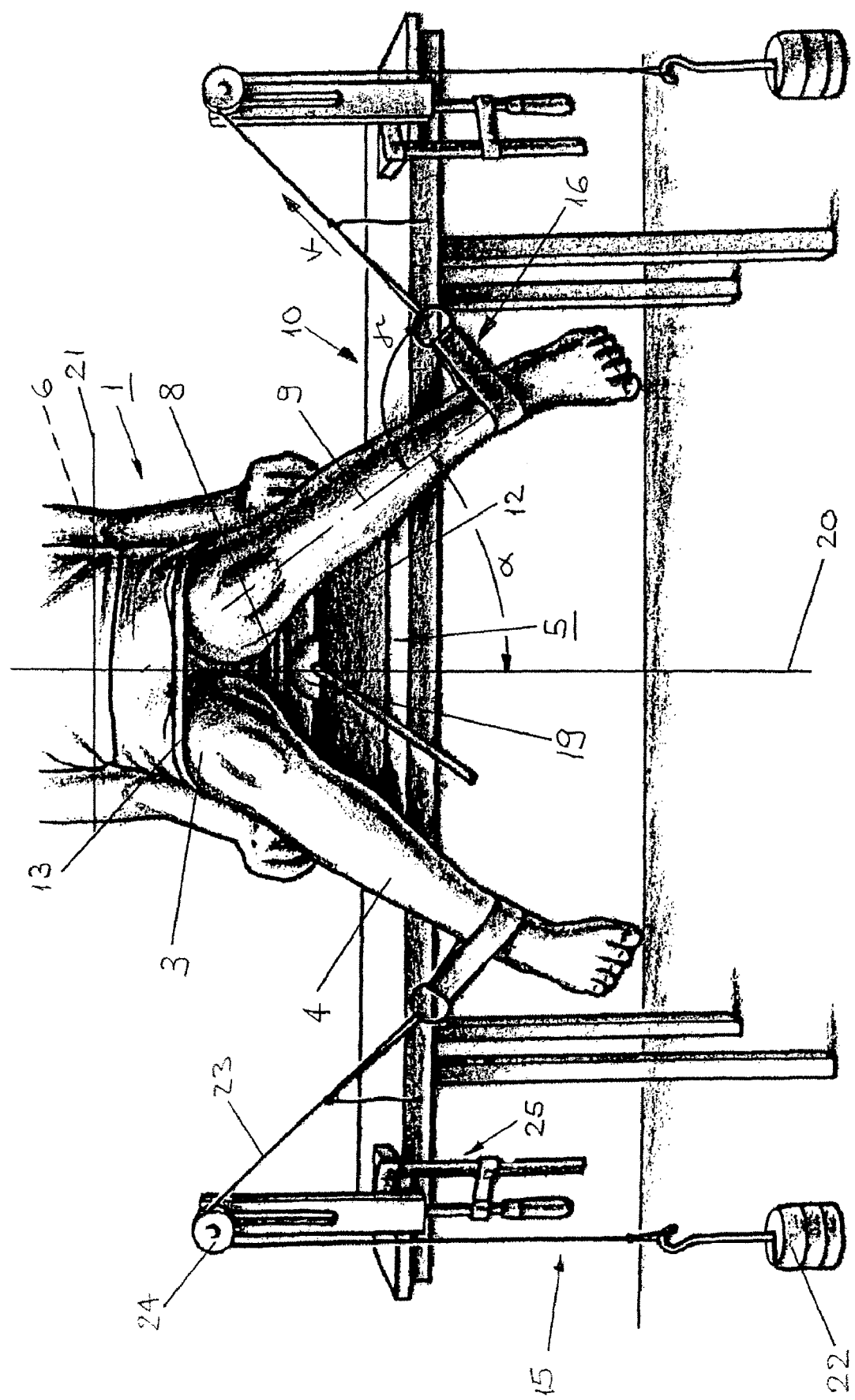

DEVICE FOR MEASURING THE INTERNAL ROTATION OF A HIP JOINT

The invention refers to a device for measuring the internal rotation of a hip joint, according to the preamble of patent claim 1.

The Japanese patent publication JP2004097489 TABUCHI discloses a medical examination table in the form of a chair, which can be adjusted in its positions with great precision, meaning the position of its backrest, its seat or its leg supports. However, it fails to disclose any measurement of the internal rotation of a hip joint.

The Russian patent No. 2 170 542 CHERNOVA discloses a process and a device to define the position of the pelvis, which measures the deflection and internal rotation of the femora in a supine position. The internal rotation is carried out in such a manner that the shinbones are turned outward by applying a suitably variable force. Apart from the internal rotation, CHERNOVA also measures the change in pelvis position depending on the rotation of the femur. The supine position also allows only a scarce fixation of the pelvis by the weight of the body.

The U.S. Pat. No. 6,773,376 DVR discloses a process to determine the internal rotation of a hip joint, wherein angle measurements are performed isokinetically by using a linear dynamometer. FIG. 5B discloses the position that the internal rotation of a hip joint is measured at. A disadvantage of this known method is the fact that an isokinetic measurement, meaning at a constant speed of motion is performed here. The aim of this process is to make a measurement purely on the muscular side, which fails to quantify the effect of bone alterations.

None of the documents mentioned above describes a measurement of the internal rotation of a hip joint by a constant force.

The object of this invention is therefore to provide a device for measuring the internal rotation of a hip joint, in particular of the angle attainable when rotating the upper thigh around its longitudinal axis by a constant force.

The measuring results thus achieved are indicative of eventual damages in the joint. At a reduced internal rotation of a hip joint, a damage of the hip joint may prematurely occur.

The invention solves the intended task through a device presenting the characteristics of claim 1.

The advantages secured by the device can essentially be seen in the fact that:
a) The patients are not resting on their backs but sit, which provides for a good fixation of the pelvis by the weight of the body; and
b) It allows examining the passive, non-active mobility (muscle force), thus making it possible to quantify, in a final phase, the degree to which an internal rotation is possible without an opposing muscular support. It also applies a defined force, so that, by detecting the femoro-acetabular collision, the effect of bone alterations can be quantified.

When applying the device according to the invention, it could further be verified that:
1) The inter- and intra-spatial reliability of the measurements according to the invention, as compared to that of a conventional measurement (not performed at a defined seating position and expenditure of effort) is excellent; and
2) A reduced internal rotation is associated with a damage in the joint. For every 10° of lesser internal rotation, the labrum degeneration revealed in an MRI rises.

In various forms of embodiment of the device according to the invention, the following devices may for instance be employed to generate a force K, where the force K is preferably applied to the lower thigh so that its effect is essentially exerted in a direction parallel to the surface of the examination table:

1) Weights that can be fastened to a tackle, for instance similar to those now commonly used for muscle training. Such devices allow generating a constant linear pulling force, which can be transferred to the lower thigh by a fixation device fastened to the ankle joint. Thanks to this pulling force exerted on the lower thigh, the latter can be turned around the longitudinal axis of the corresponding upper thigh, so that the ankle joint can be deviated from the sagittal plane and the upper thigh can be turned around its longitudinal axis by an angle $\alpha$.

2) A pushing or pulling spring, for instance a helical spring, whose spring deflection is limited by a suitable limiting device to a length s, so that upon reaching the length s, a constant force K of a desired value Z is transferred to the lower thigh by the fixation device, which is fastened to the lower thigh at the ankle joint.

3) Compressed air cylinders with a pressure limitation valve to adjust the maximally allowable pushing or pulling force. In order to transfer the pulling force, the front end of the piston rod is connected to the fixation device, so that when the pressure limitation valve acts, a force K of a desired value is transferred to the lower thigh by the fixation device, which is fastened to the lower thigh at the ankle joint.

4) An electric motor, preferably comprising a gear box, a torque limiting device and a cable winch, where one end of the tackle is fastened to the fixation device, so that thanks to the torsion limitation a constant force K of the desired value Z can be transferred to the lower thigh by the fixation device, which is fastened to the lower thigh at the ankle joint.

5) A linear electric motor with an electrically or electronically adjustable force limitation, so that thanks to the force limitation a constant force K of the desired value Z can be transferred to the lower thigh by the fixation device, which is fastened to the lower thigh at the ankle joint.

In another form of embodiment the device additionally comprises a timing device, which exemplarily includes a timepiece being readable by the operator or an electronic time run-off control integrated in the means to generate a force K. This allows that the force K is applied to the lower thigh at least during a defined minimum time lag $\Delta T > 0$. Preferably, the measurement is performed after the equilibrium of the internal rotation is reached. Thus, a time lag as great as possible is desirable to achieve an optimal result.

In another form of embodiment, the minimum time lag $\Delta T$ amounts to at least 25 seconds.

In a further form of embodiment, the means to generate a force K comprise a dynamometer.

In an additional form of embodiment, the pedestal is detachably fastened to a medical examination table.

In another form of embodiment, the means to generate a force K are detachably fastened to a medical examination table.

In a further form of embodiment, the backrest can be rotated and locked with respect to the seating surface, so that the resting surface encloses an angle $\beta$ between 85° and 95° with the seating surface. This achieves the advantage that the pelvis of the person to be examined is firmly fixated by his body weight.

In another form of embodiment, the at least one fixation device presents, as measured orthogonally to the seating surface, a selectable distance X>0 to the seating surface. The distance X is adjusted so that the force K acts on the lower thigh at a definite distance A from the center of the knee, as measured parallel to the longitudinal axis of the lower thigh. The distance A should be at least equal to the length of the lower thigh. It is advantageous to use the greatest possible distance A, though the same is limited by the height of the examination table.

In an additional form of embodiment, the line of action of the force K encloses with the normal to the seating surface lying in the sagittal plane an angle γ between 80° and 100°. This allows attaining the advantage that a force application angle of nearly 90° cannot transfer any frictional forces acting up the leg to the lower thigh.

In another form of embodiment, the value Z of the force K amounts to at least 40 Newton.

In a further form of embodiment, the means to measure an angle α between the sagittal plane and the longitudinal axis of the lower thigh of a person to be examined comprise a goniometer. In place of a goniometer, a measurement can also be performed by using one of the opto-electronic position detecting devices commonly employed in computer-assisted surgery or when using surgical navigation devices.

BRIEF DESCRIPTION OF VARIOUS FORMS OF EMBODIMENT OF THE PROCESS ACCORDING TO THE INVENTION

The process for measuring the internal rotation of a hip joint, preferably with the aid of the device according to the invention, essentially comprises the following steps:

a) Positioning of the person to be examined in a seated posture, on the seating surface of a positioning aid similar to a chair;

b) Fixation of both upper thighs of the person to be examined on the seating surface against translational motions, so that a rotation of the upper thighs around their longitudinal axis is still possible;

c) Moving the corresponding lower thighs transverse to the sagittal plane, by using a force K acting on each lower thigh at a constant value Z, so that the distal ends of the lower thighs are deviated from the sagittal plane; and d) Measuring the angle α between the sagittal plane and the longitudinal axis of the lower thigh.

An advantage of this process lies in the fact that the measuring of the internal rotation is symmetrical, meaning measured simultaneously on both hip joints of a person to be examined, so that the pelvis cannot deviate.

In a preferred form of embodiment, the force K acts on the lower thigh for a defined minimum lag of time ΔT>0.

In another form of embodiment, the minimum time lag ΔT amounts to at least 25 seconds.

A preferred form of embodiment of the process according to the invention is characterized by the fact that a statical defined force (5 kg) is to act on the lower thigh for over 30 seconds, so as to shift the same outward and thus determine an internal rotation of the hip. No active (muscle) measurements are performed, only a purely passive mobility (as a standardized screening method for an internal rotation) is examined. In addition to a weight as a defined deviating force, a linear dynamometer may also be used.

In a further form of embodiment, the adjustment of a backrest, which is moveable on the positioning aid having a resting surface for the back of the person to be examined, is done so that the resting surface encloses an angle β between 85° and 95° with the seating surface.

Another form of embodiment is characterized by the fact that the force K is purely a tensile force and acts on the lower thigh at a defined distance A, as measured in a direction parallel to the longitudinal axis of the lower thigh, from the center of the knee. The distance A should be at least equal to the length of the lower thigh. It is advantageous to use the greatest possible distance A, though the same is limited by the height of the examination table.

In a further form of embodiment, the line of action of the form K lies in a plane vertical to the sagittal plane and the transversal plane and encloses an angle γ between 8° and 100° with the longitudinal axis of the lower thigh. This achieves the advantage that a force acting angle near 90° cannot transfer any frictional forces acting up the leg to the lower thigh.

In one other form of embodiment, the value Z of the force K amounts to at least 40 Newton.

In a further form of embodiment, the measuring of the angle α performed in step d) is done by a goniometer. In place of a goniometer, a measurement can also be taken by using one of the opto-electronic position detecting devices commonly employed in computer-assisted surgery or when using surgical navigation devices. Additional possibilities to measure the angle α include a measurement of photo documentations or a mechanical-digital determination of the deviation.

In another form of embodiment, the following step is carried out prior to step a): fixating the positioning aid on a medical examination table.

The invention is in the following illustrated in even greater detail, based on the partly simplified representation of an example of embodiment.

FIG. 1 is a schematic representation of a form of embodiment of the positioning aid according to the invention, mounted on a medical examination table.

The positioning aid 5 shown in FIG. 1 essentially comprises a pedestal 12 with a seating surface 8 and a backrest 6 having a resting surface (not shown), fastening means 13 for fixating both upper thighs 3 of the person to be examined 1 to the seating surface 8 against corresponding translational motions, so that a rotation of the upper thighs 3 around their longitudinal axis (vertical to the drawing plane) is still possible, and means 15 to generate a force K parallel to an axis of action, which can unilaterally and detachably be fastened, by means of fixation devices 16, to the corresponding lower thighs 4.

The pedestal 12 of the positioning aid 5 is for instance, by means of commonly employed clamping elements (not shown), fastened to a medical examination table 10 so that the longitudinal axes of the upper thighs 3 of the person to be examined 1 extend in a direction parallel to the short side of the table surface of the examination table 10, and the lower thighs 4 project beyond one of the long sides of the table surface of the examination table and hang out freely.

In the form of embodiment pictured here, weights 22 capable of being fastened to a tackle 23 are used as means 15 for generating a force K. The tackle 23 comprises a cable and a deviating roller 24, whose distance to the examination table 10 is adjustable and which can for instance be fastened to the examination table 10 by a screw clamp 25. One end of the cable is fastened to the weights 22, while the other end of the cable is connected to the lower thigh 4 through fixation devices 16, for instance by belts fastened at the ankle joint. The form of embodiment shown here comprises, symmetrically to the sagittal plane 20, one tackle 23 each for the left leg and the right leg of the person to be examined 1.

The lower thigh 4 is, thanks to the pulling force exerted on the same, turned around the longitudinal axis of the corresponding upper thigh, so that the ankle joint is deviated from the sagittal plane 20 (vertical to the drawing surface) and the upper thigh 3 is turned around its longitudinal axis by the angle $\alpha$ Moreover, the backrest 6, which can be rotated with respect to the seating surface 8, is fixated so that its resting surface (not shown) for the back of the person to be examined 1 encloses an angle $\beta$ of 90° (not drawn) with the seating surface 8.

The measurement of the angle $\alpha$ between the sagittal surface 20 and the longitudinal axis 9 of the lower thigh 4 is performed by using the goniometer 19 set up on the pedestal 12.

The invention claimed is:

1. A device for measuring an internal rotation of a hip joint through a positioning aid comprising:
   a pedestal fitted with a seating surface and a backrest with a resting surface;
   a fastening means for fixating at least one upper thigh of a person to be examined to the seating surface against translational motions, so that a rotation of the upper thigh around its longitudinal axis is still possible;
   a means to generate a force K of a constant value Z in a direction parallel to an axis of action, that can unilaterally and detachably be fastened by means of a fixation device to a corresponding lower thigh;
   a means for measuring an angle a between the sagittal plane and the longitudinal axis of the lower thigh of the person to be examined; and
   a timing device.

2. The device according to claim 1 wherein the means for generating the force K comprises a dynamometer.

3. The device according to claim 1, wherein the pedestal can be detachably fastened to a medical examination table.

4. The device according to claim 1, wherein the means for generating the force K is detachably fastened to a medical examination table.

5. The device according to claim 1, wherein the backrest can be rotated with respect to the seating surface so that the resting surface encloses an angle $\beta$ between 85° and 95° with the seating surface.

6. The device according to claim 1, wherein the fixation device presents, measured in a direction orthogonal to the seating surface, a selectable distance X>0 to the seating surface.

7. The device according to claim 1, wherein a line of action of the force K encloses an angle $\gamma$ between 80° and 100° with the normal to the seating surface.

8. The device according to claim 1, wherein the value Z of the force K amounts to at least 40 Newton.

9. The device according to claim 1, wherein the means for generating the force K is capable of being detachably fastened to a medical examination table and comprises at least a weight, a tackle and at least one deviating roller for the tackle and wherein a first end of the tackle is connected to the weight and a second end of the tackle can be fastened to the lower thigh of the person to be examined.

\* \* \* \* \*